(12) United States Patent
Prinz et al.

(10) Patent No.: US 8,100,900 B2
(45) Date of Patent: Jan. 24, 2012

(54) SYSTEM FOR DELIVERING THERAPY

(75) Inventors: Friedrich B. Prinz, Woodside, CA (US);
Paul J. Wang, Saratoga, CA (US);
Bryant Y Lin, Menlo Park, CA (US);
Ross Venook, Burlingame, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 910 days.

(21) Appl. No.: 12/119,442

(22) Filed: May 12, 2008

(65) Prior Publication Data

US 2009/0281534 A1     Nov. 12, 2009

Related U.S. Application Data

(60) Provisional application No. 60/928,795, filed on May 11, 2007.

(51) Int. Cl.
*A61B 18/14*     (2006.01)
*A61B 18/02*     (2006.01)

(52) U.S. Cl. .......................................... 606/41; 606/20
(58) Field of Classification Search ..................... 606/41
See application file for complete search history.

(56) References Cited

U.S. PATENT DOCUMENTS 4,095,601 A * 6/1978 Aufranc et al. ................ 607/72
5,549,605 A * 8/1996 Hahnen .......................... 606/46

\* cited by examiner

*Primary Examiner* — Michael Peffley
*Assistant Examiner* — Daniel Fowler
(74) *Attorney, Agent, or Firm* — Jeffrey Schox

(57) ABSTRACT

The system of the preferred embodiments includes a first rotational element, a second rotational element, and a therapeutic source coupled to the rotational elements. The system permits simultaneous attachment to and movement around a surface of tissue, preferably during an ablation procedure (either during lesion creation or between lesion creation events), or during any other suitable procedure. The therapeutic source functions to translate along the path of tissue and deliver therapy as the first and second rotational elements rotate and roll along the path of tissue. The therapeutic source preferably delivers contiguous doses of therapy along the path of tissue. The system is preferably designed for delivering therapy to tissue and, more specifically, for delivering therapy to cardiac tissue. The system, however, may be alternatively used in any suitable environment and for any suitable reason.

29 Claims, 8 Drawing Sheets

SYSTEM FOR DELIVERING THERAPY

CROSS-REFERENCE TO RELATED APPLICATIONS

This application claims the benefit of U.S. Provisional Application No. 60/928,795, filed 11 May 2007 and entitled "Device for tissue surface navigation", which is incorporated in its entirety by this reference.

TECHNICAL FIELD

This invention relates generally to the medical device field, and more specifically to a new and useful system for delivering therapy.

BACKGROUND

Atrial Fibrillation (AF) is a cardiac arrhythmia that carries significant morbidity and mortality for greater than 2.2 million Americans. Recent studies demonstrate treatment of AF using catheter-based ablation. Ablating, or destroying the function of, tissue in different patterns in the left atrium (typically lines surrounding the pulmonary veins to block the propagation of AF triggering foci outward from the pulmonary veins) has been accepted as an effective treatment for AF. However, conventional ablation methods have many problems that have limited the efficacy of this treatment. In order to block electrical propagation, clinicians deliver energy to the tip of long thin tubes called catheters. The energy kills tissue at one point, then the catheter is to be moved to an adjacent point and energy is delivered again. This point-by-point process (conventional catheter ablation) is repeated until contiguous lines of ablated tissue are formed. As shown in FIG. 1, the posterior left atrium 100 includes pulmonary veins (LSPV, LIPV, RSPV, and RIPV). Each circular spot is a therapy delivery point of ablation 102. The pattern of ablation, as shown in FIG. 1, is one of many that clinicians use to treat AF. This conventional technique is time-consuming and requires significant skill because catheters are hard to manipulate and maneuver accurately inside a beating heart. It is difficult to: 1) place adjacent lesions and 2) maintain tissue contact (a necessity in creating a quality lesion). With significant gaps between lesions and poor tissue contact, contiguous lines of ablated tissue—and therefore effective conduction block—cannot be achieved.

Thus, there is a need in the medical device field to create a new and useful system for delivering therapy. This invention provides such improved a new and useful system.

DESCRIPTION OF THE PREFERRED EMBODIMENTS

The following description of preferred embodiments of the invention is not intended to limit the invention to these embodiments, but rather to enable any person skilled in the art to make and use this invention.

Figure 4:
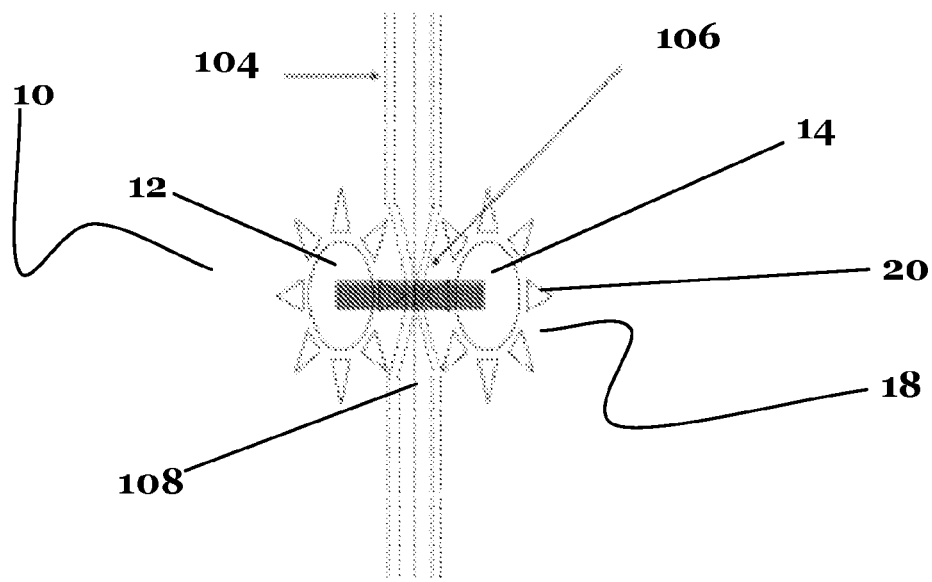
FIG. 4 is a drawing of a top view of the system of a first preferred embodiment of the invention coupled to tissue.
Figure 5:
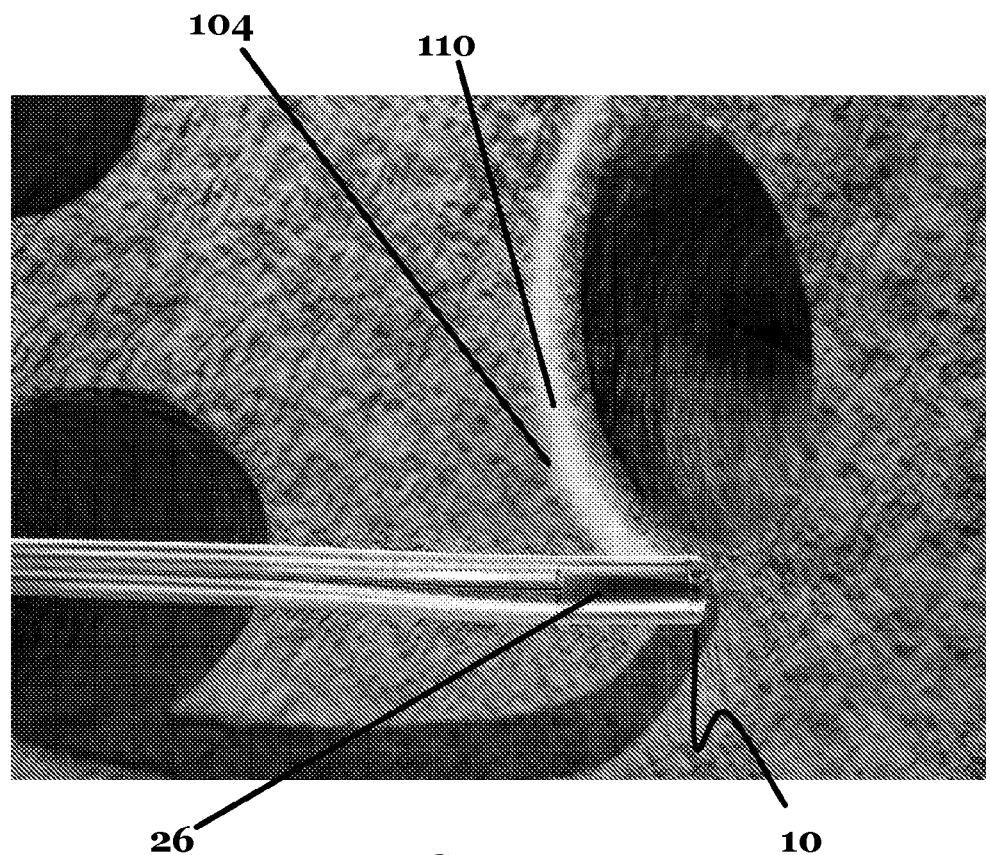
FIG. 5 is a drawing of the system of a first preferred embodiment of the invention delivering therapy to a path of tissue.
Figure 6:
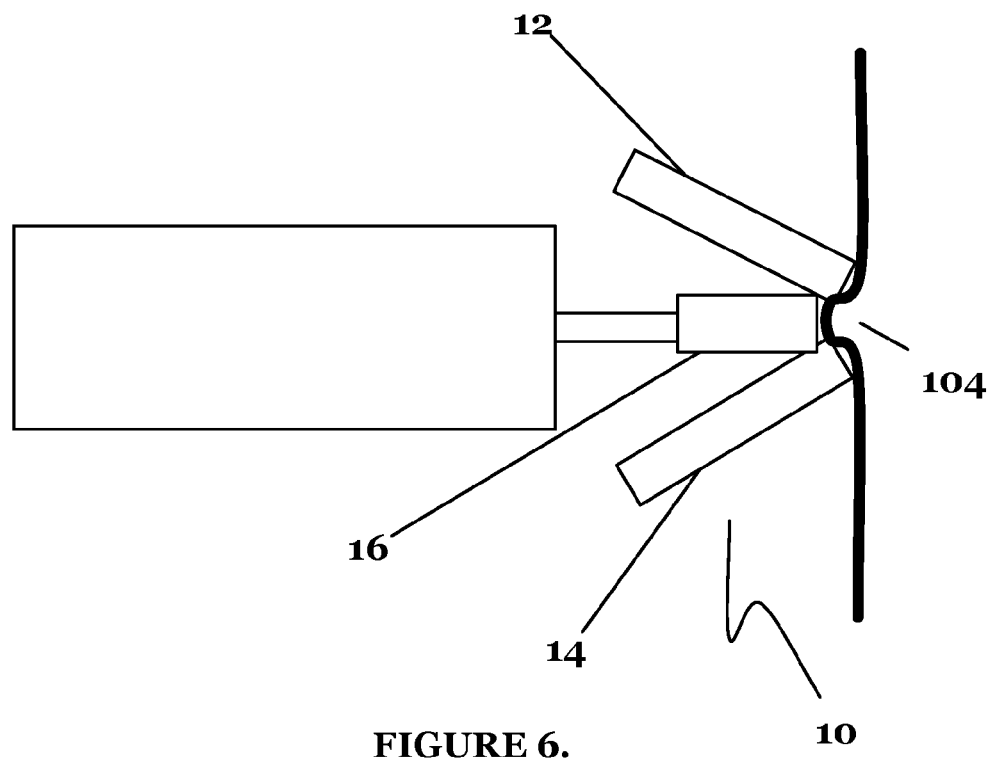
FIGS. 6 and 7 are drawings of two variations of the system of a first preferred embodiment of the invention coupled to tissue.

As shown in FIG. 6, the system 10 of the preferred embodiments includes a first rotational element 12, a second rotational element 14 coupled to the first rotational element 12, and a therapeutic source 16 coupled to the rotational elements. The system 10 permits simultaneous attachment to and movement around a surface of tissue, preferably during an ablation procedure (either during lesion creation or between lesion creation events), or during any other suitable procedure. The two rotational elements function to couple to tissue and rotate such that, as they roll along a path of tissue 104, they couple to a first portion tissue 106 and then, as they uncouple from the first portion of tissue 106, they couple to a second portion of tissue 108, as shown in FIG. 4. The therapeutic source 16 functions to translate along the path of tissue 104 and deliver therapy as the first and second rotational elements rotate and roll along the path of tissue 104. As shown in FIG. 5, the therapeutic source 16 preferably delivers contiguous doses of therapy 110 along the path of tissue 104. The system 10 is preferably designed for delivering therapy to tissue and, more specifically, for delivering therapy to cardiac tissue. The system is preferably used for treating cardiac arrhythmias, but may alternatively be used for any suitable purpose. The system 10, however, may be alternatively used in any suitable environment and for any suitable reason.

1. The Rotational Elements

Figure 1:
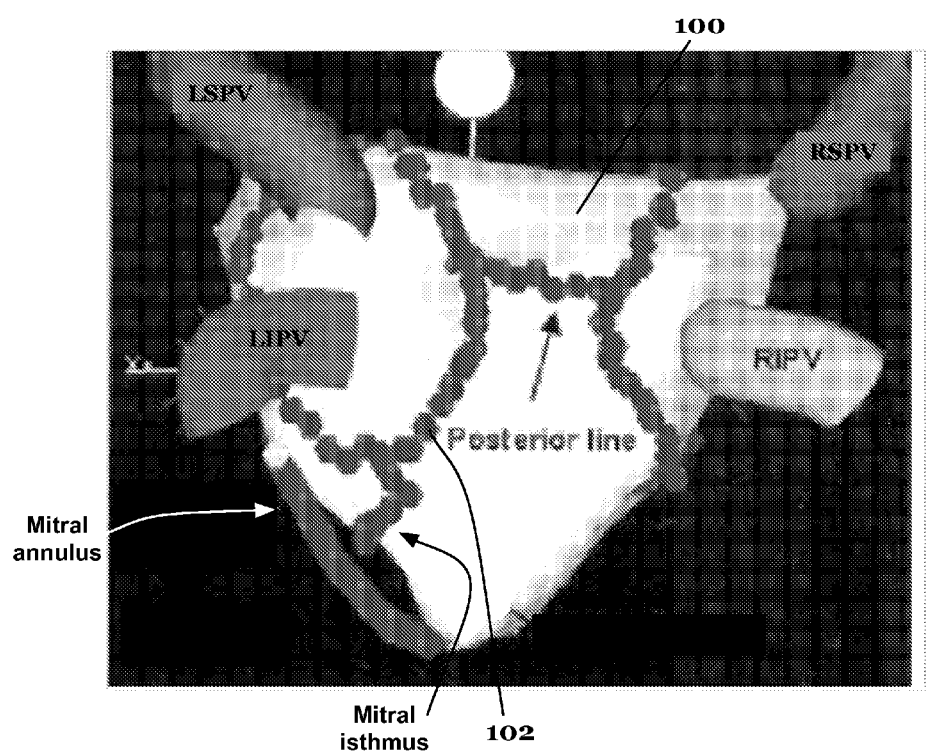
FIG. 1 is a schematic map of cardiac left atrium and pulmonary veins with therapy delivery points.
Figure 2A:
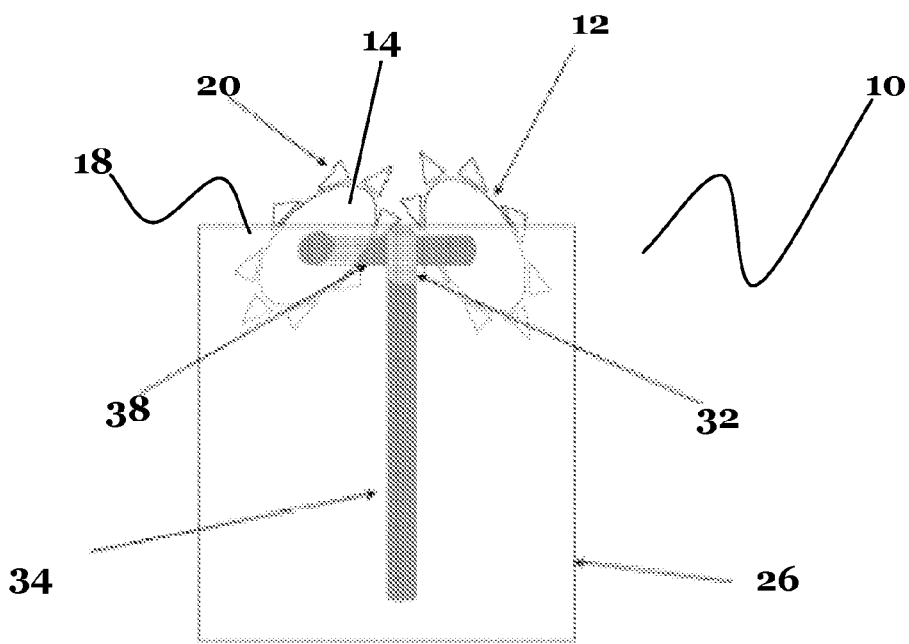
FIGS. 2A and 2B are drawings of the system of a first preferred embodiment of the invention.
Figure 2B:
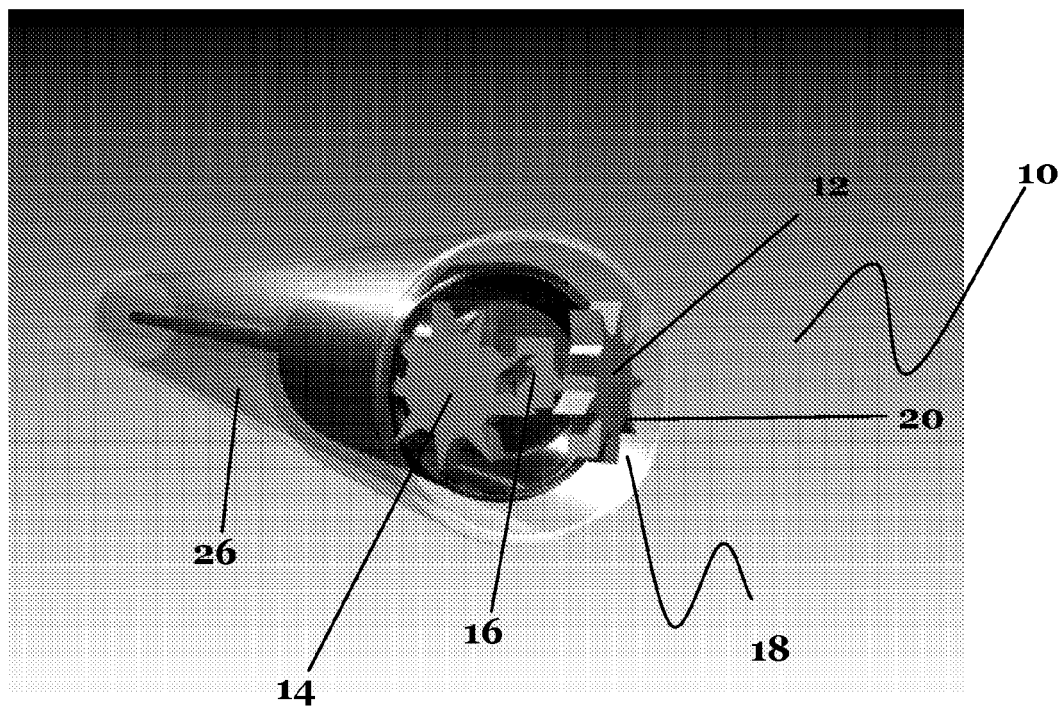

As shown in FIG. 5, the first rotational element 12 and second rotational element 14 of the preferred embodiments function to couple to tissue and rotate such that, as they roll along a path of tissue 104, they couple to a first portion tissue 106 and then, as they uncouple from the first portion of tissue 106, they couple to a second portion of tissue 108, as shown in FIG. 4. The turning or rolling of the rotational elements causes the device to roll along the tissue surface while maintaining attachment. The diameter of the rotational elements is preferably less than 5 mm and more preferably less than 3 mm, but the rotational elements may have any other suitable diameter. The rotational elements are preferably sized to function with a catheter preferably smaller than 15 French (about 5 mm) and more preferably equal to or smaller than 9 French (about 2 mm). The first rotational element 12 and the second rotational element 14 preferably do not extend beyond the diameter of the catheter when coupled to the distal portion of the catheter, as shown in FIGS. 2A and 2B. The rotational elements are preferably made from a biocompatible metal, such as stainless steel, nitinol, or platinum, but may alternatively be made from biocompatible polymers, plastic, silicon, or any other suitable material. The rotational elements are preferably manufactured using semiconductor and/or Microelectromechanical Systems (MEMS) techniques such as silicon lithography, but may alternatively be laser cut, Electrical Discharge Machined (EDM), or machined using any other suitable technique.

The first rotational element 12 and second rotational element 14 preferably couple to tissue in one of several variations. In a first variation, as shown in FIGS. 3A, 3B, 4, and 6, the first rotational element 12 is angled towards the second rotational element 14 such that the portions of the rotational elements that are coupled to and adjacent to the tissue are closer to one another than the portions of the rotational elements that are uncoupled and opposite from the tissue. In this configuration, the first rotational element cooperates with the second rotational element to pinch the tissue between the first and second rotational elements. Due to the angle of the rotational elements, the tissue becomes "pinched" (and temporarily held or coupled) between the rotational elements as the rotational elements rotate. As shown in FIG. 4, the pinching occurs because the rotational elements are further apart at the point of initial contact and closer together at the middle. As shown in FIG. 4, diagrammatic curvature lines of the tissue 104 demonstrate how the tissue 104 becomes pinched between the rotational elements.

Figure 7:
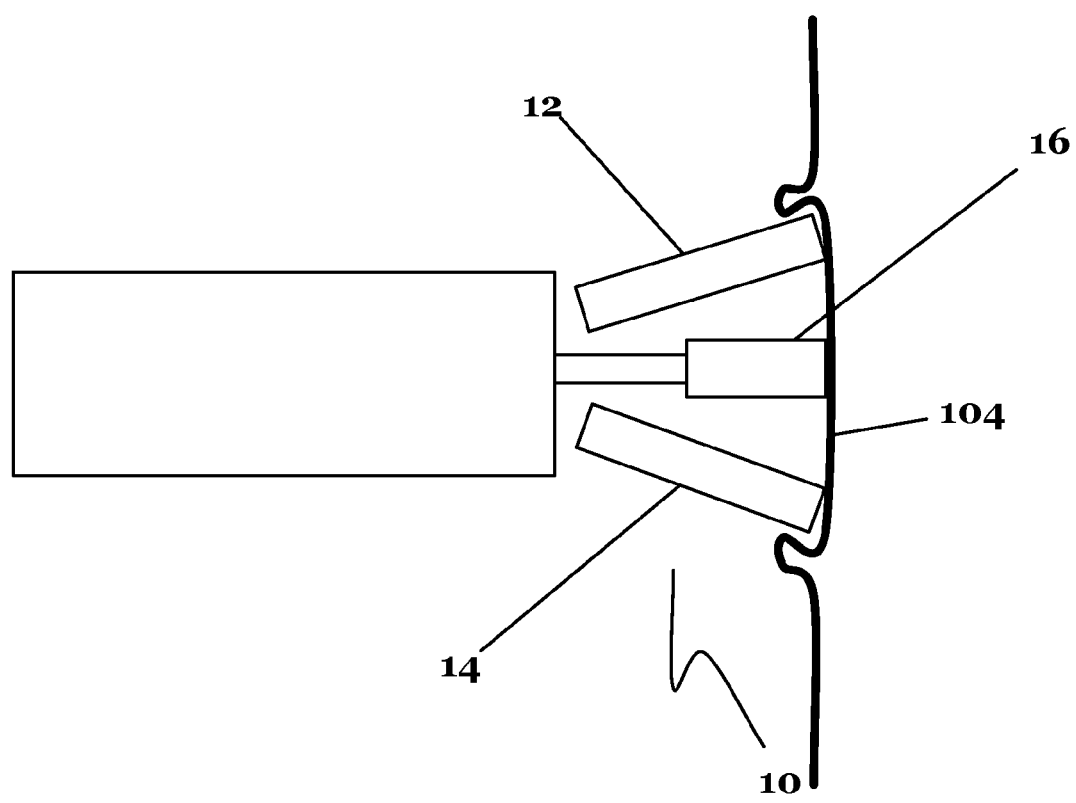

In a second variation, as shown in FIG. 7, the first rotational element 12 is angled away from the second rotational element 14 such that the portions of the rotational elements coupled to and adjacent to the tissue are further from one another than the portions of the rotational elements that are uncoupled and opposite from the tissue. In this configuration, the first rotational element cooperates with the second rotational element to push the tissue out from the first and second rotational elements. As shown in FIG. 7, the rotational elements preferably push the tissue 104 out such that it is tension and/or create a bunch of tissue at the exterior of each rotational element, which holds or couples the rotational elements to the tissue.

Figure 8:
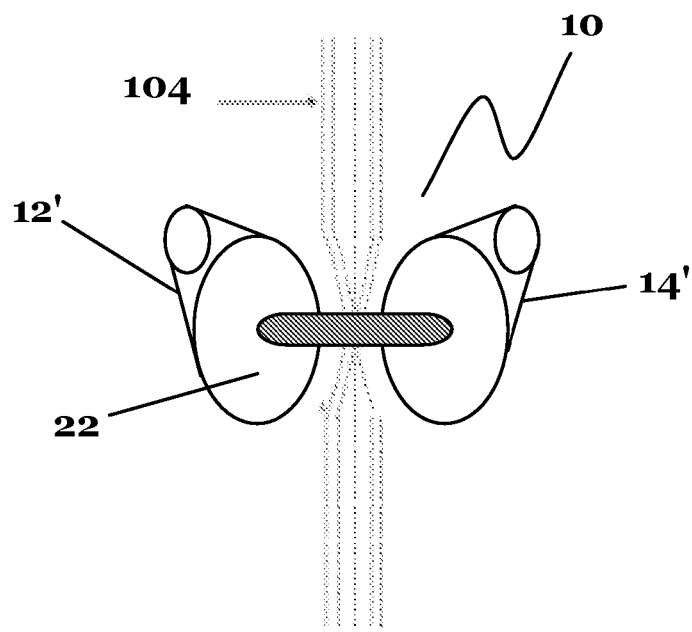
FIG. 8 is a drawing of a top view of a variation of the rotational element of the system of a first preferred embodiment of the invention.

The first rotational element 12 and second rotational element 14 are preferably one of several variations. In a first variation, as shown in FIGS. 2A and 2B, the first rotational element 12 and the second rotational element 14 are preferably wheels. The wheel is preferably cylindrically shaped, but may alternatively have any other suitable geometry. The wheel may have a flat surface that couples to the tissue, but may alternatively have an angled or textured surface to enhance the attachment of the rotational elements to the tissue. In a second variation, as shown in FIG. 8, the first rotational element 12' and the second rotational element 14' are preferably continuous tracks. The continuous tracks are preferably flexible belts, but may alternatively be a plurality of rigid units that are joined to each other. At least one sprocket 22 rotates the continuous tracks such that they travel along the path of tissue 104. The continuous tracks may have a flat surface that couples to the tissue, but may alternatively have an angled or textured surface to enhance the attachment of the rotational elements to the tissue. In a third variation, the first rotational element 12 and the second rotational element 14 are spheres or semi-spheres. Although the first rotational element 12 and the second rotational element 14 are preferably one of these three variations, the rotational elements may be any suitable element to couple to tissue and rotate. The second rotational element 14 is preferably similar, if not identical, to the first rotational element 12, but may alternatively be any suitable rotational element.

2. The Attachment Mechanisms

Figure 11:
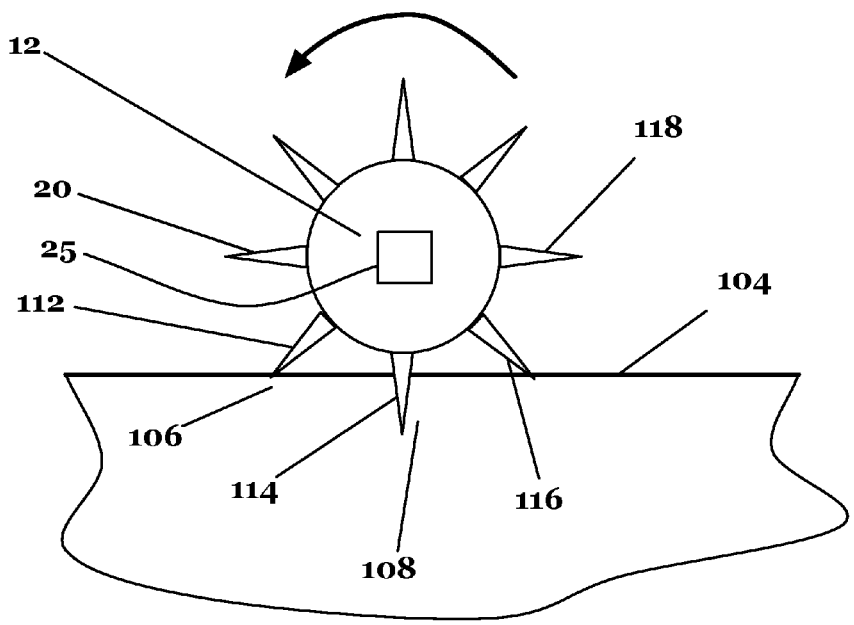
FIG. 11 is a drawing of the modes of the attachment elements of the system.
Figure 12:
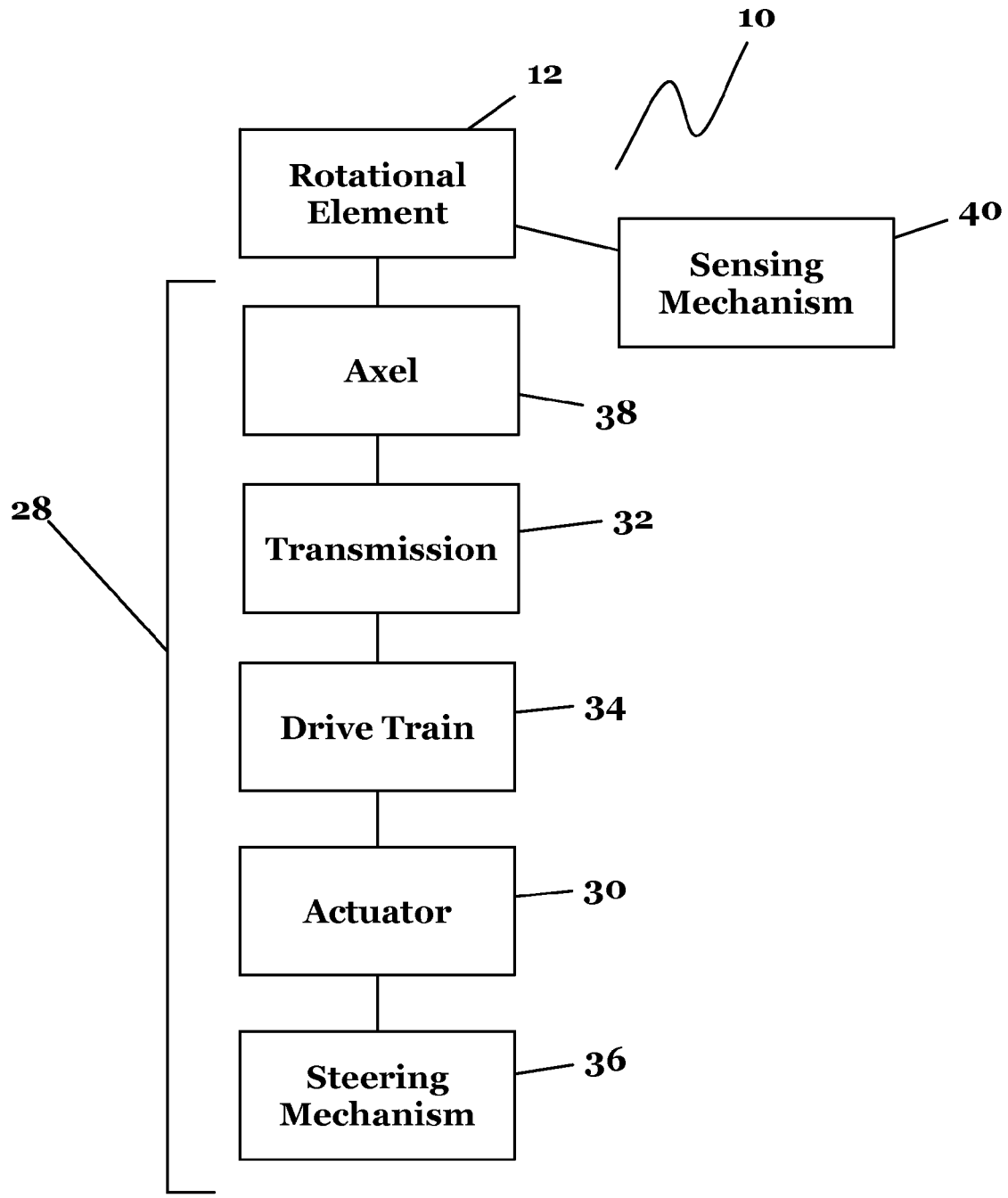
FIG. 12 is a schematic drawing of the driving mechanism and sensing mechanism of the system.

As shown in FIGS. 2A and 2B, the rotational elements of the preferred embodiments also include at least one attachment mechanism 18. The attachment mechanism 18 includes a plurality of attachment elements 20 that attach to the tissue 104. The attachment elements 20 of each attachment mechanism 18 are preferably arranged around the circumference of each rotational element such that as the rotational elements rotate, at least one attachment element 20 attaches to the path of tissue 104, but may alternatively be arranged in any other suitable fashion. As shown in FIG. 11, the attachment elements 20 preferably transition through the following modes as the rotational elements rotate: grasp mode 112—the attachment element 20 comes in contact with tissue 104 and begins to attach to the tissue 104; attached mode 114—the attachment element 20 is attached to the tissue 104; release mode 116—the attachment element 20 begins to release the tissue 104; and unattached mode 118—the attachment element 20 is not attached to the tissue 104. As the attachment elements 20 (coupled to the rotational elements) roll along a path of tissue 104, they couple to a first portion tissue 106 and then, as they uncouple from the first portion of tissue 106, they couple to a second portion of tissue 108, as shown in FIG. 11. As the rotational elements rotate and roll along the tissue and the attachment elements 20 are attaching and un-attaching from the tissue 104 as described above, preferably at least one attachment element is always in attached mode such that the system 10 simultaneously attaches to and moves around a surface of tissue 104. The attachment mechanisms 18 preferably function to optimize attachment while balancing the need to remove the system 10 from the tissue 104 with minimal tissue effect or damage.

Figure 3A:
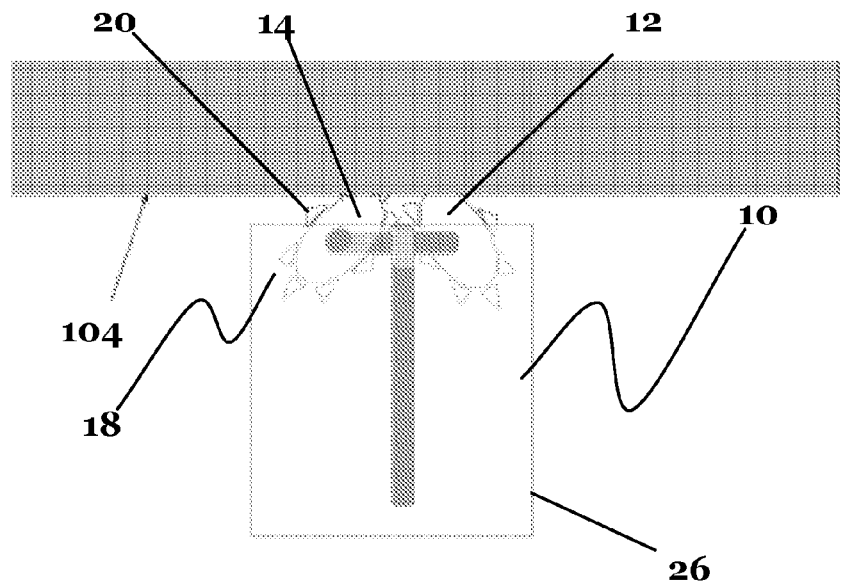
FIGS. 3A and 3B are drawings the system of a first preferred embodiment of the invention coupled to tissue.
Figure 3B:
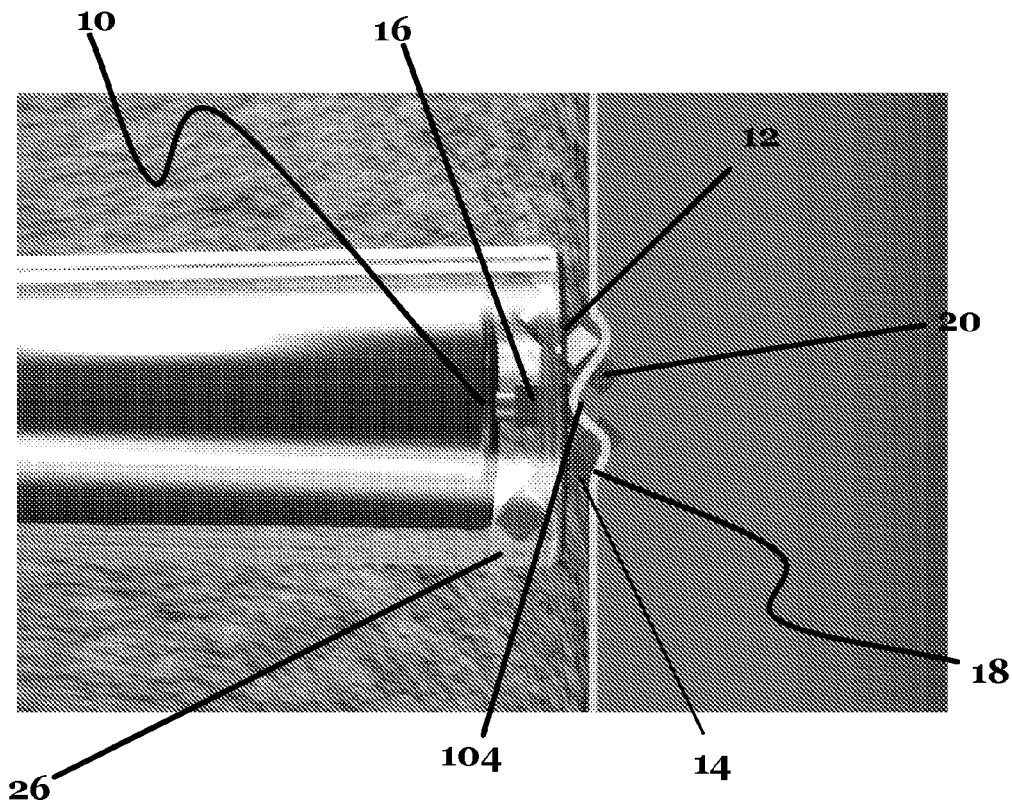
Figure 9:
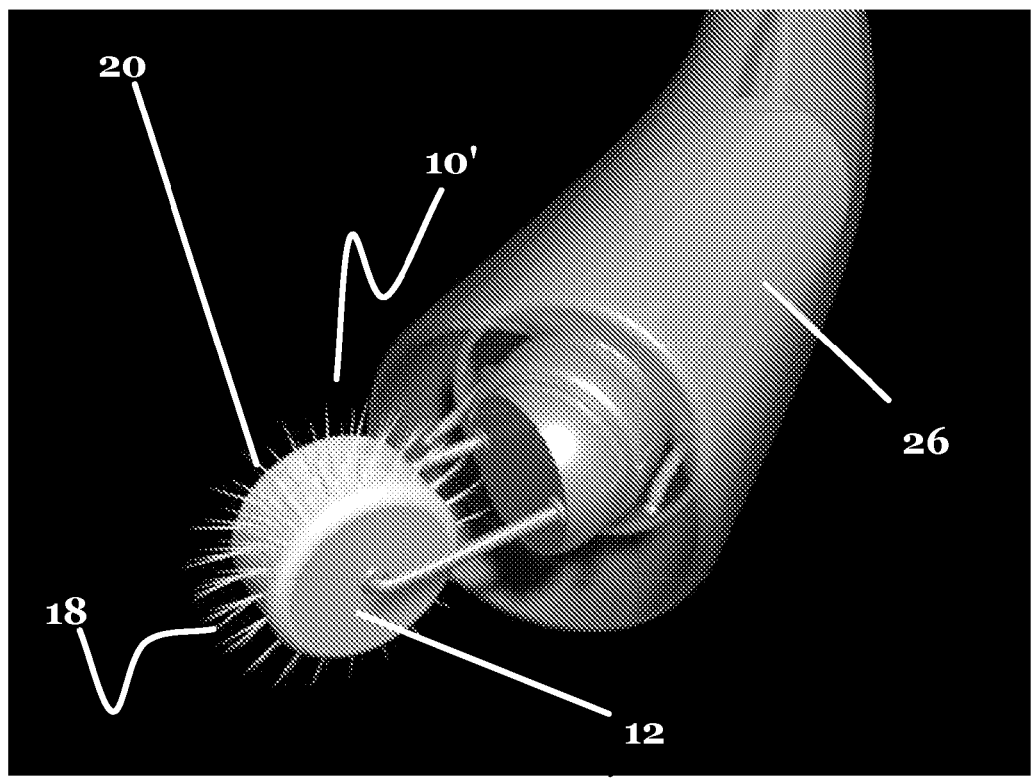
FIG. 9 is a drawing of the system of a second preferred embodiment of the invention.

The attachment mechanisms 18 are preferably one of several variations. In a first variation, as shown in FIGS. 2A-3B, the attachment mechanism includes a plurality of attachment elements 20 that are protrusions. The protrusions preferably function such that at least a portion of the protrusion penetrates the tissue 104, as shown in FIGS. 3A and 3B. When the system 10 is in contact with the tissue 104, the protrusions penetrate a short distance into the tissue 104 to create better surface attachment through the orientation of the rotational elements, the orientation of the protrusions and the geometry of the protrusions. The pinching action between the protrusions preferably enhances the attachment force of the rotational elements to the tissue 104. The protrusions preferably have a triangular cross-section and at least one sharp edge, but may alternatively have any other suitable geometry, such as spikes or barbs. The protrusions are preferably designed such that there is a high protrusion length to rotational element diameter ratio and are preferably arranged around the rotational element such that there is sufficient spacing to allow each individual protrusion to penetrate the tissue. The protrusions may alternatively have any suitable length and be in any other suitable arrangement. In this variation, the attachment elements 20 may be of the same or different material from the rotational elements, and may be metallic, plastic, or any other suitable material. The attachment mechanisms 18 and attachment elements 20 are preferably manufactured using semiconductor and/or Microelectromechanical Systems (MEMS) techniques such as silicon lithography, but may alternatively be laser cut, Electrical Discharge Machined (EDM), or machined using any other suitable technique. The protrusions may be on a macro scale (having a length greater than one hundred microns and less than five millimeters) or on a micro scale (having a length less than one hundred microns). The micro scale protrusions may additionally attach to the tissue due to friction and the large number of attachment elements 20 coupled to the rotational element 12, as shown in FIG. 9.

Figure 10:
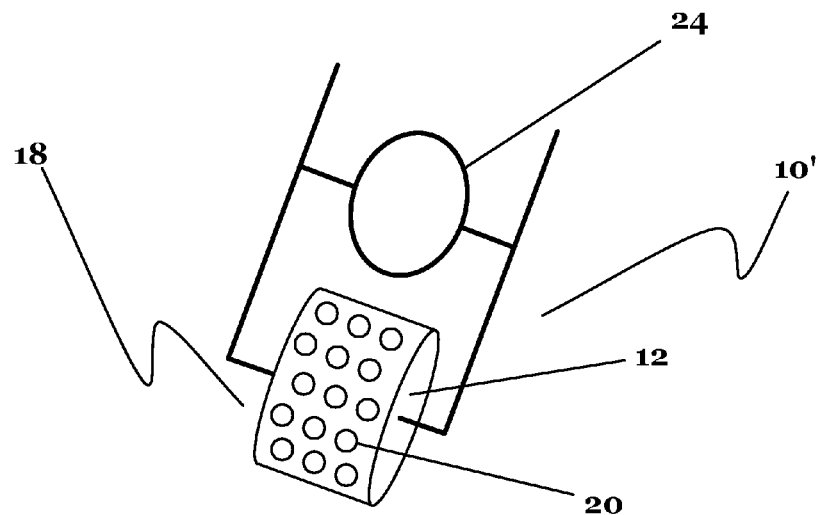
FIG. 10 is a drawing of a variation of the attachment mechanism of the system of a second preferred embodiment of the invention.

In a second variation, as shown in FIG. 10, attachment mechanism 18 includes a vacuum device 24 and the attachment elements 20 are holes defined by the rotational element 12. The vacuum device 24 preferably applies a suction force to the holes such that the rotational element attaches to the tissue 104 due to the suction force and pulls it against the rotational element 12. In this variation, the suction force can be applied to a subset of the attachment elements 20 to create zones of attachment of the tissue to the rotational element. In a third variation, as shown in FIG. 11, the attachment mechanism includes a cooling device 25. The cooling device 25 preferably cools the attachment elements 20 and/or the rotational elements such that tissue 104 attaches to the attachment elements 20 and/or the rotational elements due to the tissue freezing to the attachment elements 20 and/or the rotational elements. In this variation, the cooling can be applied to a subset of the attachment elements 20 or to portions of the rotational elements to create zones of attachment to the tissue. The cooling device 25 preferably cools the attachment elements 20 and/or the rotational elements to at least less than zero degrees Celsius. Additionally, heating may subsequently be applied to the attachment elements 20 and/or the rotational elements such that tissue 104 detaches from the attachment elements 20 and/or the rotational elements. The heating is preferably due to a radiofrequency current, but may alternatively be due to running open or closed (internal) irrigation of a fluid such as saline or any other suitable heating source.

Although the attachment mechanism 18 and attachment elements 20 are preferably one of these three variations or any combination thereof, the attachment mechanism 18 and attachment elements 20 may be any suitable mechanism or element to attach to tissue and/or enhance the attachment of the rotational elements to tissue, such as a sticky substance such as adhesives, suction cups, high friction materials, or a device that utilizes Van der Waals forces.

3. The Therapeutic Source

The therapeutic source 16 of the preferred embodiments is coupled to the rotational elements and functions to translate along the path of tissue 104 and deliver therapy as the rotational elements rotate and roll along the path of tissue 104. As shown in FIG. 5, the therapeutic source 16 preferably delivers contiguous doses of therapy 110 along the path of tissue 104. The therapeutic source preferably delivers therapy to the tissue in one of several variations. In a first variation, the therapeutic source delivers therapy to the tissue directly through the rotational elements. In this variation, the rotational elements and/or attachment mechanisms are a conductive material such as metal, but may alternatively be any other suitable material. In a second variation, the therapeutic source is adjacent to the rotational elements and delivers the therapy to the tissue directly, bypassing the rotational elements.

The therapy delivered by the therapeutic device 16 is preferably one of several variations. In a first variation, the therapy is ablation therapy. Ablation therapy preferably destroys the function of the tissue and/or of the cells that make up the tissue. Ablation therapy is preferably delivered in one of several versions. A first version is radiofrequency current. Radiofrequency current can be delivered to the tissue with, or without internal or external fluid irrigation. A second version is Cryotherapy and a third version is ultrasound such as High Intensity Focused Ultrasound (HIFU). Ablation therapy may also be delivered through microwaves, chemicals (such as ethanol), radiation, and lasers. Although the ablation therapy is preferably delivered in one of these versions, it may alternatively be delivered in any other suitable form. In a second variation, the therapy is biologic delivery. Biologic therapy preferably includes the delivery of drugs, tissue, stem cells, or any other suitable biologic. In a third variation, the therapy is device delivery. Device delivery therapy preferably includes the delivery of devices such as wireless pacing elements, pacing or defibrillating leads, and/or artificial conductions systems. Although the therapeutic source 16 and the therapy delivered by the source are preferably one of these variations, the therapeutic source 16 may deliver any suitable therapy in any suitable fashion or configuration.

4. Second Preferred Embodiment

As shown in FIGS. 9 and 10, the system 10' of the second embodiment is nearly identical to the system 10 of the first embodiment. The difference between the two embodiments, however, is that the system 10' of the second embodiment includes a single rotational element. In this embodiment, the rotational element 12 preferably includes an attachment mechanism 18. The attachment mechanism 18 preferably includes a plurality of attachment elements 20 that attach to the tissue 104. The system in further alternative embodiments may include three or any other suitable number of rotational elements with or without attachment mechanisms.

5. Additional Elements

The system 10 of the preferred embodiments also includes a catheter 26. As shown in FIGS. 2B and 5. The rotational elements are preferably coupled to the distal portion of the catheter 26. The catheter 26 is preferably a standard catheter, but may alternatively be any other suitable catheter. The system 10 preferably includes a catheter for intravascular procedures and a catheter or thoracoscopic tool for epicardial use. The catheter 26 is preferably steerable through magnetism, robotics, guide wires, or any other suitable mechanism. The catheter may also include a handle, sensors, electrodes, multiple lumens, multiple ports, radio-opaque parts, any other suitable elements, and any combination thereof. The catheter 26 is preferably smaller than 15 French (about 5 mm) and more preferably equal to or smaller than 9 French (about 2 mm).

The system 10 of the preferred embodiments also includes a driving mechanism 28, which extends into or through the catheter 26 and connects to the rotational elements and functions to drive the rotational elements. The driving mechanism 28 includes any of the following in any suitable combination: an actuator 30 that actuates the rotational elements, a transmission 32 that translates motion from the actuator into rotational motion of the rotational elements, a drive shaft 34 that transfers motion from the actuator to the transmission, a steering mechanism 36 that steers the rotational elements, and an axle 38 that transfers the rotational motion from the transmission to the rotational elements. The driving mechanism 28 preferably drives the rotational elements to move the system 10 at a velocity preferably between 0.1 mm to over 100 cm per minute, but may alternatively move the system 10 at any other suitable velocity.

The actuator 30 of the preferred embodiments is preferably a manual actuator or an electric motor, but may alternatively be any other suitable actuator such as a hydraulic motor, a pneumatic motor, a magnetic actuator, and any combination thereof. The actuator may be a miniature actuator (such as a Squiggle motor—New Scale Technologies), contained within the catheter, but may alternatively be larger and contained in the portion of the catheter outside the body or in a module that attaches to the catheter.

The steering mechanism 36 of the preferred embodiments is preferably one of several variations. In a first variation, the steering mechanism steers the rotational elements through the torquing or movement of the catheter 26. In a second variation the steering mechanism 36 utilizes differential driving of the rotational elements such that the rotational elements are driven at different speeds relative to one another such that the system 10 turns towards the rotational element that is rotating at a slower speed. In a third variation, the steering mechanism 36 includes a steering column coupled to the axle that changes the direction of the axle to steer the rotational elements. In the third variation, the steering column is preferably a guide wire that the can be torqued or manually operated from outside the body.

The system 10 of the preferred embodiments also includes a sensing mechanism 40, coupled to the rotational elements. The sensing mechanism 40 is preferably selected from the group consisting of mapping electrodes, impedance electrodes, temperature probes, ultrasound and any combination thereof. The sensing mechanism can map voltage and timing, can assess ablation efficacy, and can perform any other suitable operation.

The system 10 of the preferred embodiments also includes a navigation system. The navigation system preferably utilizes any suitable navigation system including CARTO, NAVx, Fluoroscopy, MRI/CT guidance, and DynaCT (Siemens). The navigation system may further utilize preprogrammed paths to perform a procedure and/or mapping.

Although omitted for conciseness, the preferred embodiments include every combination and permutation of the various rotational elements, the various attachment mechanisms and attachment elements, the various therapeutic sources, the various catheters, and the various driving mechanisms.

As a person skilled in the art will recognize from the previous detailed description and from the figures and claims, modifications and changes can be made to the preferred embodiments of the invention without departing from the scope of this invention defined in the following claims.

We claim:

1. A system for delivering therapy to tissue, comprising:
   a first rotational element;
   a second rotational element coupled to the first rotational element, wherein the two rotational elements are adapted to couple to tissue and rotate such that they couple to a first portion of tissue and then, as they uncouple from the first portion of tissue, they couple to a second portion of tissue, wherein the first portion of tissue and the second portion of tissue are along a path of tissue; and
   a therapeutic source, coupled to the rotational elements, that is adapted to translate along the path of tissue and deliver therapy as the first and second rotational elements rotate.

2. The system of claim 1, wherein the therapeutic source is adapted to deliver therapy to the tissue through at least one of the first rotational element and the second rotational element.

3. The system of claim 1 wherein the therapy delivered by the therapeutic source is ablation therapy and the therapeutic source is adapted to deliver contiguous doses of ablation therapy along the path of tissue.

4. The system of claim 3, wherein the ablation therapy is delivered as radiofrequency current.

5. The system of claim 1 wherein the first and second rotational elements are belts.

6. The system of claim 1 wherein the first and second rotational elements are wheels.

7. The system of claim 6, wherein the first rotational element is angled towards the second rotational element such that the portions of the rotational elements coupled to the tissue are a first distance from one another and the portions of the rotational elements uncoupled from the tissue are a second distance from one another, wherein the first distance is less than the second distance such that the first rotational element cooperates with the second rotational element to pinch the tissue between the first and second rotational elements.

8. The system of claim 6, wherein the first rotational element is angled away from the second rotational element such that the portions of the rotational elements coupled to the tissue are a first distance from one another and the portions of the rotational elements uncoupled from the tissue are a second distance from one another, wherein the first distance is greater than the second distance such that the first rotational element cooperates with the second rotational element to push the tissue out from the first and second rotational elements.

9. The system of claim 1, further comprising:
   a first attachment mechanism circumferentially disposed on the first rotational element; and
   a second attachment mechanism circumferentially disposed on the second rotational element, wherein each attachment mechanism includes a plurality of attachment elements, and as the rotational elements rotate, at least one attachment element is adapted to attach to the path of tissue.

10. The system of claim 9 wherein at least one of the first and second attachment mechanisms includes a vacuum device and at least one of the first and second rotational elements defines a plurality of holes, wherein a suction force is applied by the vacuum device to the holes such that the at least one rotational element attaches is adapted to attach to the tissue due to the suction force.

11. The system of claim 9 wherein at least one of the first and second attachment mechanisms includes a cooling device, and wherein a subset of attachment elements on the at least one attachment mechanism is configurable to be cooled to less than zero degrees Celsius such that the subset of attachment elements attaches to the tissue due to the tissue freezing to the subset of attachment elements.

12. The system of claim 9 wherein the plurality of attachment elements are a plurality of protrusions, wherein at least a portion of a protrusion is adapted to penetrate the tissue.

13. The system of claim 12 wherein the plurality of protrusions have a length less than one hundred microns.

14. A system for delivering therapy to tissue, comprising:
    a catheter;
    a first rotational element coupled to a distal portion of the catheter;
    second rotational element coupled to the first rotational element, wherein the two rotational elements are adapted to rotate along a path of tissue and cooperatively couple to the tissue along the path of tissue;
    a therapeutic source, coupled to the distal portion of the catheter, that is adapted to translate along the path of tissue and deliver therapy as the first and second rotational elements rotate; and
    a driving mechanism, coupled to the catheter and to the rotational elements, that drives the rotational elements.

15. The system of claim 14, wherein the driving mechanism includes at least one of an actuator that actuates the rotational elements and a transmission that translates motion from the actuator into rotational motion of the rotational elements.

16. The system of claim 15, wherein the driving mechanism further includes at least one of a drive shaft that transfers motion from the actuator to the transmission and a steering mechanism that steers the rotational elements.

17. The system of claim 14 further comprising a sensing mechanism, coupled to the rotational elements, selected from the group consisting of mapping electrodes, impedance electrodes, temperature probes, and any combination thereof.

18. The system of claim 14, wherein the therapeutic source is adapted to deliver therapy to the tissue through the rotational element.

19. The system of claim 14 wherein the therapy delivered by the therapeutic source is ablation therapy and the therapeutic source is adapted to deliver contiguous doses of ablation therapy along the path of tissue.

20. The system of claim 19, wherein the ablation therapy is delivered as radiofrequency current.

21. The system of claim 14, further comprising:
a first attachment mechanism circumferentially disposed on the first rotational element; and
a second attachment mechanism circumferentially disposed on the second rotational element, wherein each attachment mechanism includes a plurality of attachment elements, and as the rotational elements rotate, at least one attachment element is adapted to attach to the path of tissue.

22. The system of claim 21, wherein the plurality of attachment elements are a plurality of protrusions, wherein at least a portion of a protrusion is adapted to penetrate the tissue.

23. A system for delivering therapy to tissue, comprising:
a first rotational element that is adapted to roll along a path of tissue;
a first attachment mechanism circumferentially disposed on the first rotational element, having a plurality of first attachment elements, wherein each first attachment element is adapted to transition through the following modes:
grasp mode, wherein the first attachment element comes in contact with tissue and begins to attach to the tissue;
attached mode, wherein the first attachment element is attached to the tissue;
release mode, wherein the first attachment element begins to release the tissue; and
unattached mode, wherein the first attachment element is not attached to the tissue;
a second rotational element that is adapted to roll along the path of tissue;
a second attachment mechanism circumferentially disposed on the second rotational element, having a plurality of second attachment elements, wherein each second attachment element is adapted to transition through the following modes:
grasp mode, wherein the second attachment element comes in contact with tissue and begins to attach to the tissue;
attached mode, wherein the second attachment element is attached to the tissue;
release mode, wherein of second attachment element begins to release the tissue; and
unattached mode, wherein of second attachment element is not attached to the tissue;
wherein, as the first and second rotational elements roll along the path of tissue, at least one attachment element is in the attached mode; and
a therapeutic source, coupled to the rotational element, that is adapted to translate along the path of tissue and deliver therapy as the rotational element rolls along the path of tissue.

24. The system of claim 23, wherein the second attachment mechanism and the second rotational element cooperate with the first attachment mechanism and the first rotational element to attach to the path of tissue.

25. The system of claim 23 wherein the plurality of first and second attachment elements are a plurality of protrusions, wherein at least a portion of a protrusion is adapted to penetrate the tissue.

26. The system of claim 25 wherein the plurality of protrusions have a length greater than one hundred microns and less than five millimeters.

27. The system of claim 25 wherein the plurality of protrusions have a length less than one hundred microns.

28. The system of claim 23, wherein the therapeutic source is adapted to deliver therapy to the tissue through the rotational element.

29. The system of claim 23, wherein the therapy delivered by the therapeutic source is ablation therapy and the therapeutic source is adapted to deliver contiguous doses of ablation therapy along the path of tissue.

* * * * *

UNITED STATES PATENT AND TRADEMARK OFFICE
CERTIFICATE OF CORRECTION

| | |
|---|---|
| PATENT NO. | : 8,100,900 B2 |
| APPLICATION NO. | : 12/119442 |
| DATED | : January 24, 2012 |
| INVENTOR(S) | : Friedrich B. Prinz et al. |

It is certified that error appears in the above-identified patent and that said Letters Patent is hereby corrected as shown below:

In column 10, line 15, "of" should read --the--
In column 10, line 17, "of" should read --the--

Signed and Sealed this
First Day of May, 2012

David J. Kappos
*Director of the United States Patent and Trademark Office*